(12) United States Patent
Lafian

(10) Patent No.: US 10,352,840 B2
(45) Date of Patent: Jul. 16, 2019

(54) MOISTURE MONITORING APPARATUS AND METHOD INCLUDING A TENSIOMETER

(71) Applicant: Jesse Lafian, Athens, GA (US)

(72) Inventor: Jesse Lafian, Athens, GA (US)

( * ) Notice: Subject to any disclaimer, the term of this patent is extended or adjusted under 35 U.S.C. 154(b) by 125 days.

(21) Appl. No.: 15/724,315

(22) Filed: Oct. 4, 2017

(65) Prior Publication Data

US 2018/0080861 A1 Mar. 22, 2018

Related U.S. Application Data

(63) Continuation-in-part of application No. 15/495,961, filed on Apr. 24, 2017, now abandoned.

(60) Provisional application No. 62/404,076, filed on Oct. 4, 2016, provisional application No. 62/326,410, filed on Apr. 22, 2016.

(51) Int. Cl.
| | | |
|---|---|---|
| *G01N 9/10* | (2006.01) | |
| *G01L 1/00* | (2006.01) | |
| *G01N 3/02* | (2006.01) | |
| *G01N 7/10* | (2006.01) | |
| *G01N 13/04* | (2006.01) | |
| *G01N 33/24* | (2006.01) | |
| *G01L 9/00* | (2006.01) | |
| *G01N 13/02* | (2006.01) | |
| *G01N 19/10* | (2006.01) | |

(52) U.S. Cl.
CPC .............. *G01N 13/04* (2013.01); *G01L 1/005* (2013.01); *G01L 9/0041* (2013.01); *G01L 9/0051* (2013.01); *G01N 7/10* (2013.01); *G01N 13/02* (2013.01); *G01N 19/10* (2013.01); *G01N 33/246* (2013.01); *G01N 2033/245* (2013.01)

(58) Field of Classification Search
CPC ............. G01N 13/04; G01N 2033/245; G01N 33/246; G01N 13/02; G01N 7/10; G01N 19/10; G01L 9/0041; G01L 9/0051; G01L 1/005; A01G 25/167
See application file for complete search history.

(56) References Cited

U.S. PATENT DOCUMENTS

| | | | | |
|---|---|---|---|---|
| 4,909,070 A | * | 3/1990 | Smith | G01N 27/225 324/663 |
| 4,953,389 A | * | 9/1990 | Schurch | G01N 13/02 73/64.48 |
| 2012/0079876 A1 | * | 4/2012 | Stroock | G01N 13/02 73/64.51 |

\* cited by examiner

*Primary Examiner* — Brandi N Hopkins
(74) *Attorney, Agent, or Firm* — White-Welker & Welker, LLC; Matthew T. Welker, Esq.

(57) ABSTRACT

An elongated apparatus that measures soil water tension is disclosed, having a hydrogel chamber for receiving a plurality of macro-sized hydrogel particles through its open side and a sealed inner wall, the hydrogel held in the hydrogel chamber by a durable, hydrophilic, and porous window secured to the open side of the hydrogel chamber. The window, when the apparatus is received in soil, transmits moisture between the soil and the hydrogel chamber, causing variable pressure within the hydrogel chamber that can be converted to a measurement of soil water tension on the opposite side of the window. This pressure produces various mechanical effects, measurable by various types of sensors within the elongated probe. A method for measuring soil water tension at multiple depths within a soil profile is also disclosed.

21 Claims, 13 Drawing Sheets

MOISTURE MONITORING APPARATUS AND METHOD INCLUDING A TENSIOMETER

CROSS REFERENCE TO RELATED APPLICATIONS

This application is a Continuation-In-Part of co-pending U.S. patent application Ser. No. 15/495,961, entitled "Tensiometer", filed Apr. 27, 2017.

U.S. patent application Ser. No. 15/495,961 is a non-provisional of U.S. Provisional Patent Application Ser. 62/326,410, entitled "Tensiometer", filed Apr. 22, 2016.

This application is a non-provisional of U.S. Provisional Patent Application Ser. 62/404,076, entitled "Tensiometer", filed Oct. 4, 2016. The benefit under 35 USC § 119(e) of the United States provisional application is hereby claimed, and the aforementioned applications are hereby incorporated herein by reference.

FEDERALLY SPONSORED RESEARCH

Not Applicable

SEQUENCE LISTING OR PROGRAM

Not Applicable

TECHNICAL FIELD OF THE INVENTION

The present invention relates generally to tensiometers. More specifically, the present invention relates to affordable, ultra-low-maintenance tensiometers and methods to improve irrigation efficiency, thereby helping ensure future water supply, water quality, and agricultural productivity.

BACKGROUND OF THE INVENTION

Water conservation is becoming increasingly important. As global temperatures increase, drought limits the water supply to farms, cities, industries, and ecosystems. Over-irrigation can contribute to water shortages, plant/crop loss, and pollution caused by agro-chemical runoff. Improving irrigation efficiency would provide environmental and economic benefits worldwide.

One way to reduce over-irrigation is to irrigate based on measurement and monitoring of soil water tension (SWT)—the degree to which soil water adheres to soil particles. There are different types of instruments used to measure SWT; however, such instruments have drawbacks that constrict usage for irrigation purposes for homes and office complexes and for farming or other large area irrigation monitoring and control. A primary drawback arises from the high expense of current options.

For large area irrigation control, a single instrument does not represent a significant portion of the overall cost, but such large areas typically require SWT reports from multiple locations and at a plurality of discrete depths for evaluating water availability around root growth extending into the soil.

Accordingly, there is a need in the art for an affordable, ultra-low-maintenance SWT monitoring apparatus and method to measure SWT that can improve irrigation efficiency, thereby promoting large-scale agricultural productivity and environmental stewardship.

DEFINITIONS

Hydrogel—a network of chemically- or physically-cross-linked polymers that are hydrophilic. Hydrogels are highly absorbent; they can contain over ninety percent water.

Load cell—a transducer that converts force into a measurable electrical output. Although there are many varieties of load cells, strain gauge based load cells are the most commonly used type.

MEMS (microelectromechanical systems) pressure sensor—a type of pressure sensor approximately thirty cubic millimeters in size.

LVDT (linear variable differential transformer)—a common type of electromechanical transducer that can convert the displacement of an object to which it is coupled mechanically into a corresponding electrical signal. LVDT linear position sensors are readily available that can measure movements as small as a few millionths of an inch up to several inches.

Proximity sensor—a sensor able to detect the presence of nearby objects without any physical contact. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors. For example, a capacitive or photoelectric sensor might be suitable for a plastic target; an inductive proximity sensor always requires a metal target.

Soil water tension (SWT)—a variable that quantifies how strongly or weakly soil water is held by soil particles. SWT is used to accurately determine when plants/crops need to be irrigated.

Tensiometer—a device for measuring soil water tension.

SUMMARY OF THE INVENTION

The present invention meets the need in the art for an affordable, ultra-low-maintenance apparatus and method for measuring soil water tension (SWT) as an indicative factor in evaluating irrigation requirements.

The present invention of a SWT monitoring apparatus comprises (1) an elongated probe having at least one tensiometer and (2) a battery-powered head unit that attaches to the elongated probe and collects data from the tensiometer(s) in the elongated probe.

Each tensiometer within the elongated probe comprises a hydrogel chamber having an inner wall and an open side, hydrogel comprising a plurality of millimeter-sized hydrophilic particles received into the hydrogel chamber through its open side, and a durable, hydrophilic, and porous window attached to the elongated probe in sealing closing relation overlying the open side of the hydrogel chamber and an inner face of the window in bearing contact with a portion of the hydrogel for holding the hydrogel within the hydrogel chamber. A sensor is secured to the elongated probe in sensing relation to the hydrogel chamber.

When the apparatus is inserted into a selected location in a ground surface to dispose the elongated probe and its tensiometer(s) below the surface of the soil, pressure within the hydrogel chamber increases as the hydrogel absorbs water from the soil proximal to the window (when SWT is low); conversely, pressure within the hydrogel chamber decreases as the soil proximal to the window absorbs water from the hydrogel (when SWT is high).

The sensor produces a variable signal in response to a mechanical effect originating from the degree of pressure within the hydrogel chamber, which can be correlated to and thus converted to a degree of SWT, and communicates the signal to a microcontroller in the head unit which converts the signal to a determined SWT value at a soil depth associated with the tensiometer and communicates this value to a display screen or remote transmission module. This enables soil irrigation decisions to be informed by evaluation of an observed SWT detected by the SWT monitoring apparatus disposed in a ground location.

In another aspect, the present invention provides a method for acquiring SWT data for evaluating whether to irrigate, comprising the steps of:

(a) providing an apparatus including an elongated probe with at least one tensiometer, each tensiometer comprising:
  a hydrogel chamber formed in the elongated probe and having an inner wall and an open side;
  hydrogel comprising a plurality of millimeter-sized hydrophilic particles received into the hydrogel chamber through its open side;
  a durable, hydrophilic, and porous window attached to the elongated probe in sealing closing relation overlying the open side of the hydrogel chamber and an inner face of the window in bearing contact with a portion of the hydrogel for holding the hydrogel within the hydrogel chamber; and
  a sensor secured to the elongated probe in sensing relation for evaluating a mechanical effect originating from the pressure within the hydrogel chamber based on the amount of water absorbed by the hydrogel into the hydrogel chamber through the window;

(b) providing a second part of the apparatus, a head unit (that connects to the elongated probe such as by mated threads, press fit, or similar, providing a leak proof joinder of the two components) comprising:
  batteries to power the apparatus;
  a microcontroller to control the apparatus such as by determining when the apparatus enters battery-saving mode and when the apparatus exits battery-saving mode to collect and communicate a signal from a sensor within a tensiometer in the elongated probe;
  a circuit board for connecting the electronics of the apparatus; and
  a remote transmission module (for when remote data transmission is needed); or
  a display screen (for when remote data transmission is not needed)

(c) inserting the apparatus into a selected location in a ground surface to dispose the elongated probe and its tensiometer(s) below the surface of the soil;

(d) acquiring from the sensor within a tensiometer a variable signal based on a mechanical effect originating from pressure within the hydrogel chamber corresponding to variable SWT in the soil proximal to the window;

(e) displaying on a display screen within the head unit or sending via a remote transmission module within the head unit a determined SWT at a soil depth associated with a respective tensiometer, whereby soil irrigation decisions are directed by an evaluation of an observed SWT detected by the apparatus disposed in a ground location.

Other objects, advantages and features of the present invention may be readily determined upon a reading of the following detailed description of the invention in conjunction with the drawings and the appended claims.

BRIEF DESCRIPTION OF THE DRAWINGS

The accompanying drawings, which are incorporated herein and form a part of the specification, illustrate the present invention and its various embodiments and, together with the description, further explain the principles of the invention and enable a person skilled in the pertinent art to make and use the invention.

DETAILED DESCRIPTION OF THE INVENTION

In the following detailed description of the exemplary embodiments of the invention, reference is made to the accompanying drawings (where like numbers refer to like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the present invention.

Figure 9:
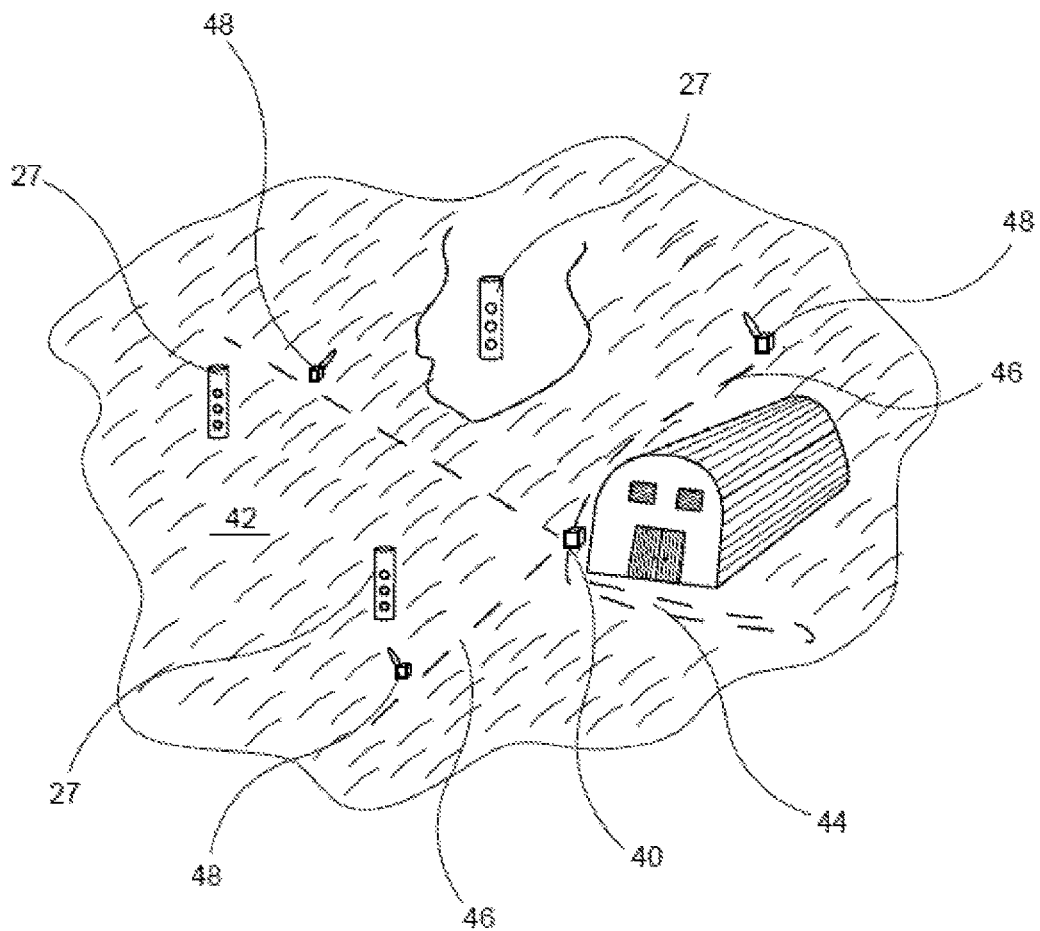
FIG. 9 illustrates a plurality of the apparatuses of the present invention interconnected with an automated irrigation control system having branches and remote water sprayers for home, office complex, and farm irrigation.

The apparatus of the present invention improves accessibility to SWT data, thereby enabling landscapers, commercial growers, and others to accurately determine when irrigation is needed. The apparatus also improves irrigation-scheduling processes. As illustrated in FIG. 9, one or more elongated probes 27 are readily interconnect with an automated irrigation control system 40 for use in settings that require irrigation 42 (e.g., lawns, gardens, nurseries, greenhouses, farms, and research generally). The automated irrigation control system 40 connects to a pipe 44 from a supply of water and to distribution branches 46 having irrigation spray nozzles 48. By optimizing the volume of water used for irrigation, the present invention improves irrigation efficiency.

Figure 10:
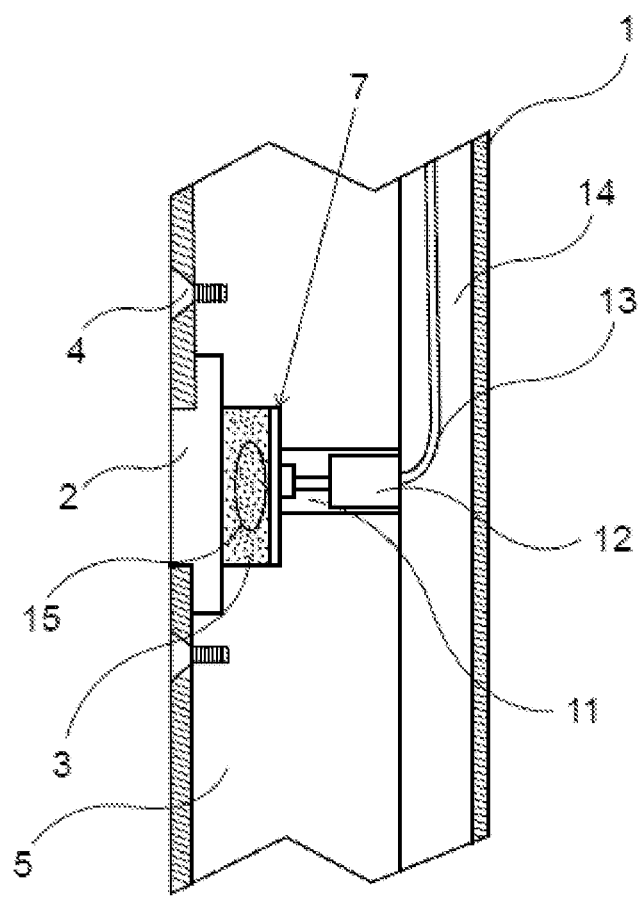
FIG. 10 illustrates a close-up side cross-sectional view of a second embodiment of the elongated probe of the present invention which includes an LVDT. This figure shows how a tensiometer of this second embodiment (comprising an LVDT, flexible barrier, hydrogel, hydrogel chamber, and window) is constructed.
Figure 11:
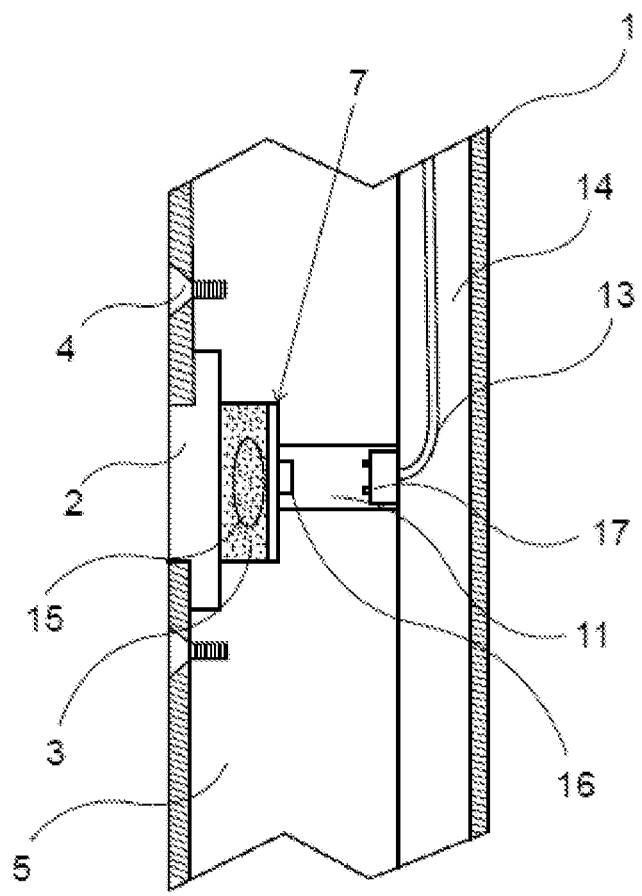
FIG. 11 illustrates a close-up side cross-sectional view of a third embodiment of the elongated probe of the present invention which includes a proximity sensor. This figure shows how a tensiometer of this third embodiment (comprising a proximity sensor, target plate, flexible barrier, hydrogel, hydrogel chamber, and window) is constructed.
Figure 12:
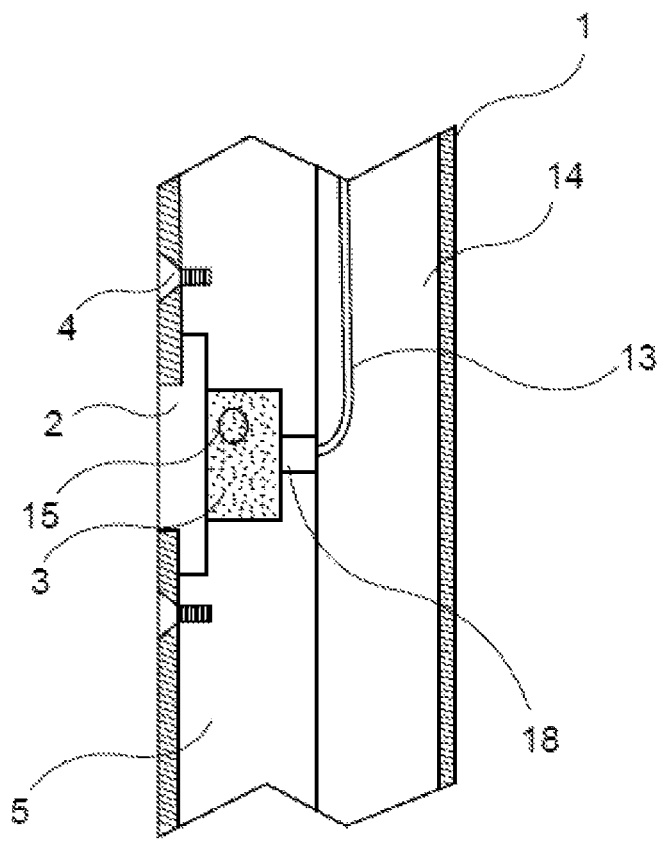
FIG. 12 illustrates a close-up side cross-sectional view of a fourth embodiment of the elongated probe of the present invention which includes a MEMS pressure sensor. This figure shows how a tensiometer of this fourth embodiment (comprising a MEMS pressure sensor, hydrogel, hydrogel chamber, and window) is constructed.

Within the elongated probe 27 of the present invention, hydrogel 15 (as seen in FIGS. 10-12), received in the hydrogel chamber 3, swells or shrinks depending on the moisture proximal to it. In settings where soil water is weakly bound to soil particles (i.e., where SWT is low), the hydrogel 15 in the hydrogel chamber 3 absorbs moisture that passes through a window 2 from soil proximal to the window. Conversely, in soil environments where water is strongly bound to soil particles (i.e., where SWT is high), the soil absorbs moisture that passes through the window 2 from the hydrogel 15 in the hydrogel chamber 3.

The hydrogel expands while absorbing moisture from the soil, but the window 2 seals the hydrogel chamber 3, constricting the expansion of the hydrogel causing the hydrogel to pressurize the hydrogel chamber. This variable pressure produces a mechanical effect that is sensed by a sensor proximal to a hydrogel chamber. This signal is based on and thus can be converted to SWT. A measurement of SWT indicates how strongly soil water is held by soil particles, and thus how easily soil water can be acquired by plant roots. This information can be used to inform irrigation scheduling, enabling agricultural productivity and efficient water usage.

The apparatus of the present invention consists of an elongated probe, of which there are four distinct embodiments, that connects to a probe-agnostic battery-powered head unit. The elongated probe consists of an outer and inner frame holding at least one tensiometer including a window, hydrogel chamber, hydrogel, and a sensor. The inner frame defines the hydrogel chamber which has an open side and the inner wall. After hydrogel is received into the hydrogel chamber, a durable, hydrophilic, and porous window closes the open side of the hydrogel chamber. The window enables transmission of water between the soil and the hydrogel in the hydrogel chamber. A sensor is secured to the inner frame in sensing relation to the hydrogel chamber. An outer frame secures to the inner frame that holds the components of one or more tensiometers disposed in spaced-apart relation within the elongated probe.

The sensor detects a variable signal in response to a mechanical effect originating from the degree of pressure within the hydrogel chamber that holds hydrogel (depending on the volume of soil water absorbed by the hydrogel) and communicates this signal to a microcontroller within the head unit of the apparatus. The signal is converted to a SWT measurement via a microcontroller within the head unit and either sent via a remote transmission module within the head unit (when remote data transmission is needed) or displayed on a screen within the head unit (when remote data transmission is not needed).

A first embodiment of the elongated probe 27 (illustrated in FIGS. 3-8), uses a load cell 9 as a sensor. The tensiometer 11 of this embodiment comprises a load cell 9 (attached to an inner frame 5 by a pair of screws 10), a dowel pin 8, a flexible barrier 7, a hydrogel chamber 3, hydrogel 15, and a window 2.

Figure 1:
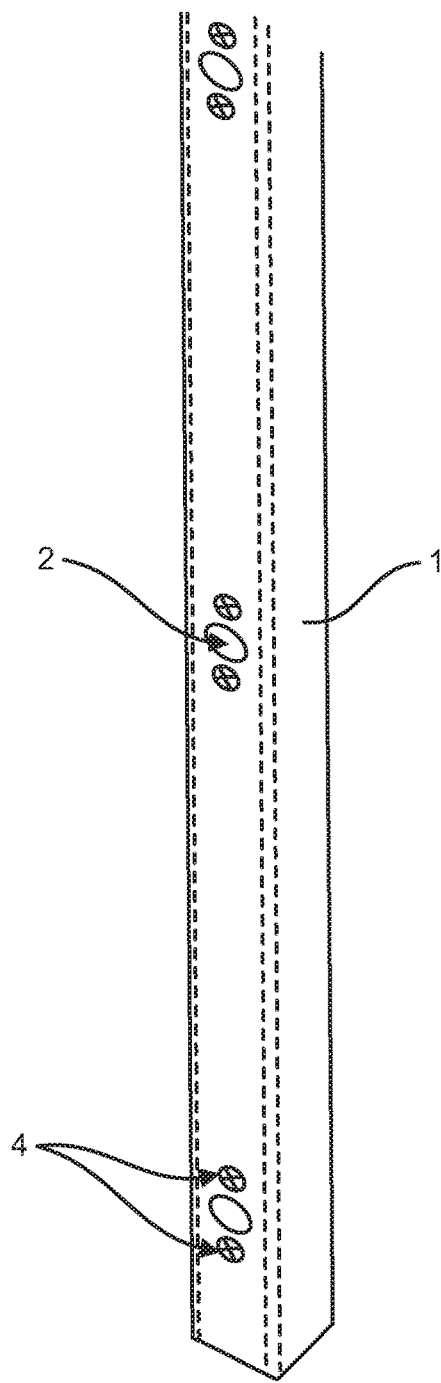
FIG. 1 illustrates an assembled elongated probe of the present invention and three windows, each of which is part of a discrete tensiometer, disposed in spaced-apart relation within the elongated probe.
Figure 2:
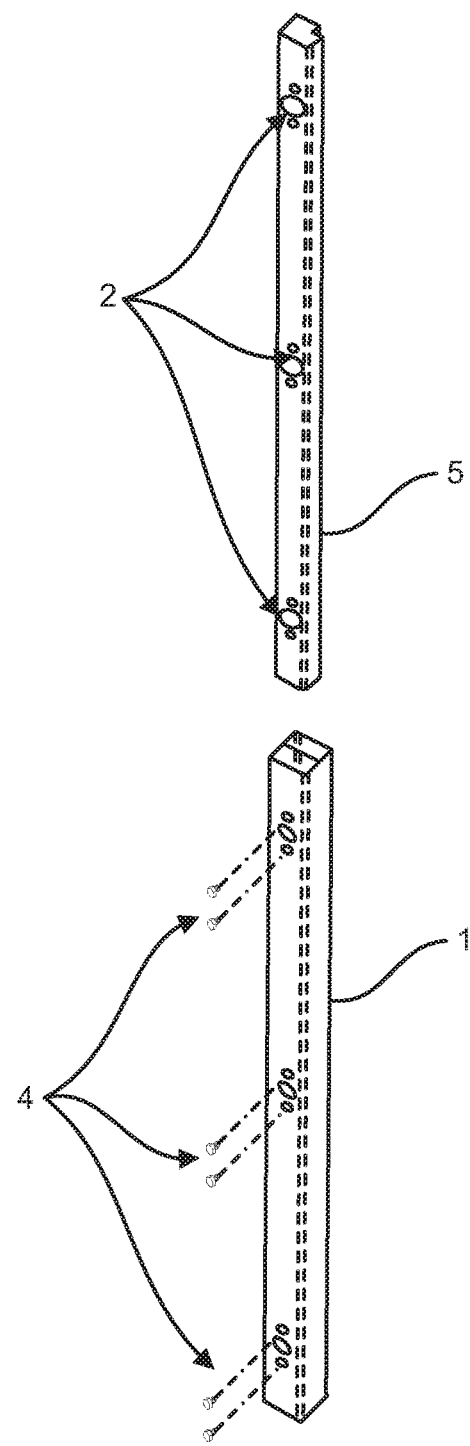
FIG. 2 illustrates an expanded view of the inner and outer frames of the elongated probe.
Figure 3:
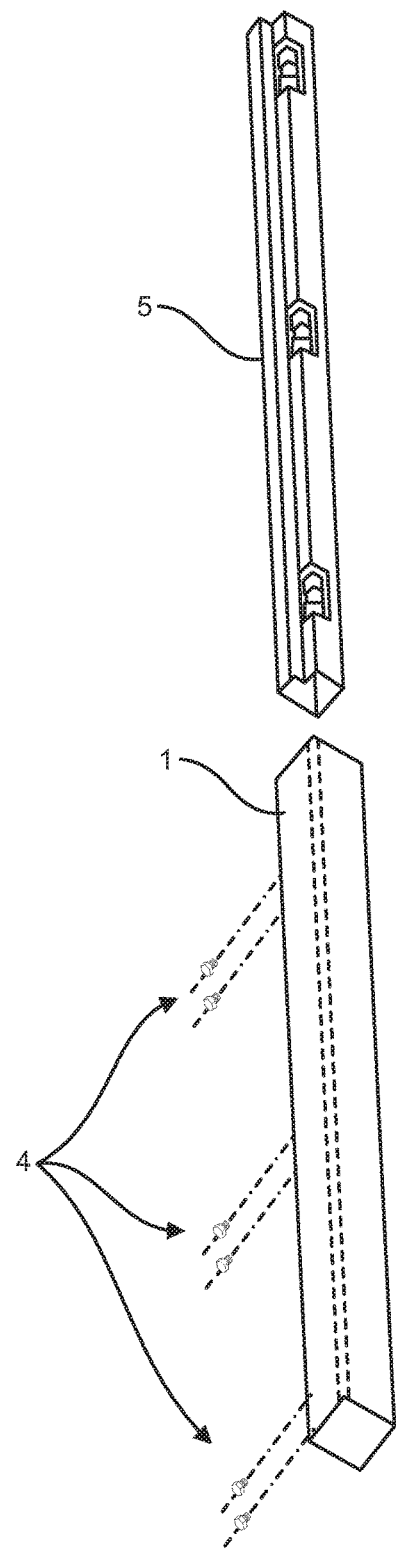
FIG. 3 illustrates an opposing expanded view of the inner and outer frames of the elongated probe, revealing a first embodiment of the elongated probe which includes a load cell that attaches to the inner frame.
Figure 4:
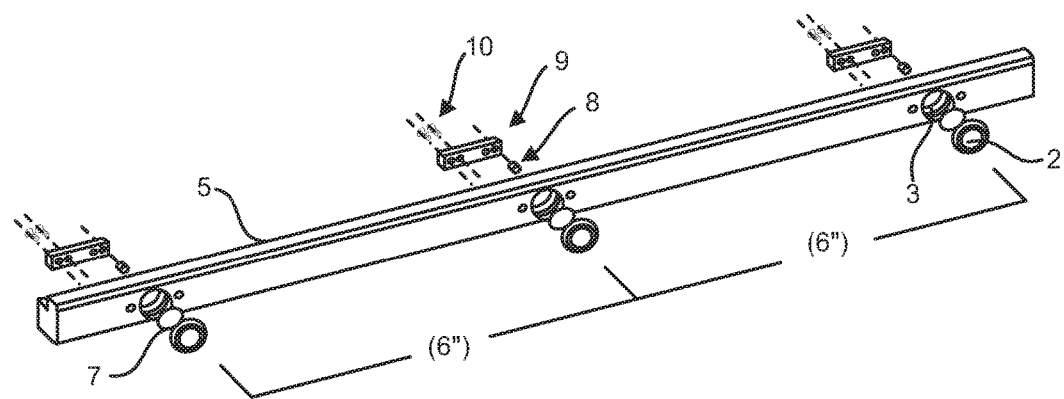
FIG. 4 illustrates an expanded view of the inner frame of the first embodiment of the elongated probe, revealing how three tensiometers of this embodiment (each including a load cell, dowel pin, flexible barrier, hydrogel chamber, and window) are constructed.
Figure 5:
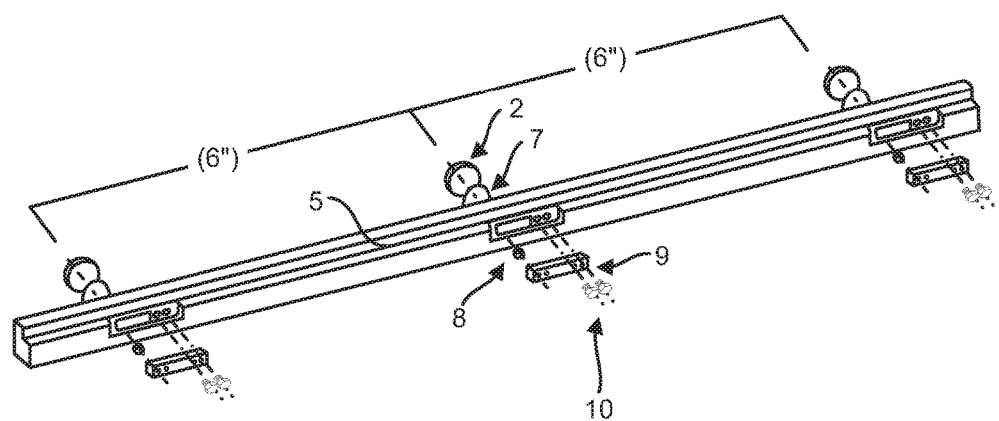
FIG. 5 illustrates an opposing expanded view of the inner frame of the first embodiment of the elongated probe, revealing how three tensiometers of this embodiment (each including a load cell, dowel pin, flexible barrier, hydrogel chamber, and window) are constructed.
Figure 6A:
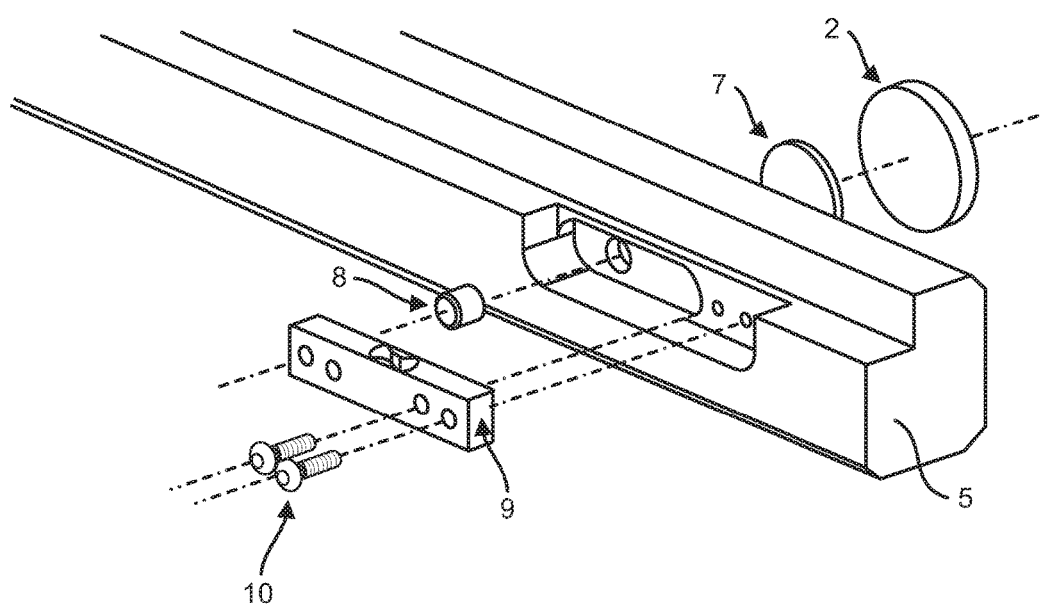
FIG. 6A illustrates a close-up, expanded view of the inner frame of the first embodiment of the elongated probe, revealing how an individual tensiometer of this embodiment (including a load cell, dowel pin, flexible barrier, hydrogel chamber, and window) is constructed.
Figure 6B:
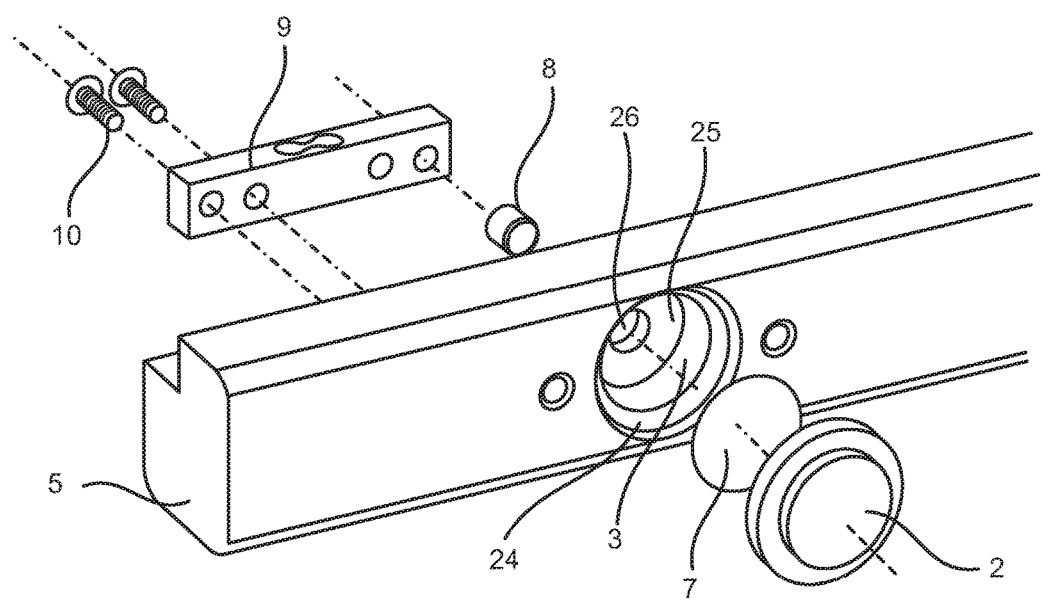
FIG. 6B illustrates an opposing close-up, expanded view of the inner frame of the first embodiment of the elongated probe, revealing how an individual tensiometer of this embodiment (including a load cell, dowel pin, flexible barrier, hydrogel chamber, and window) is constructed.
Figure 7:
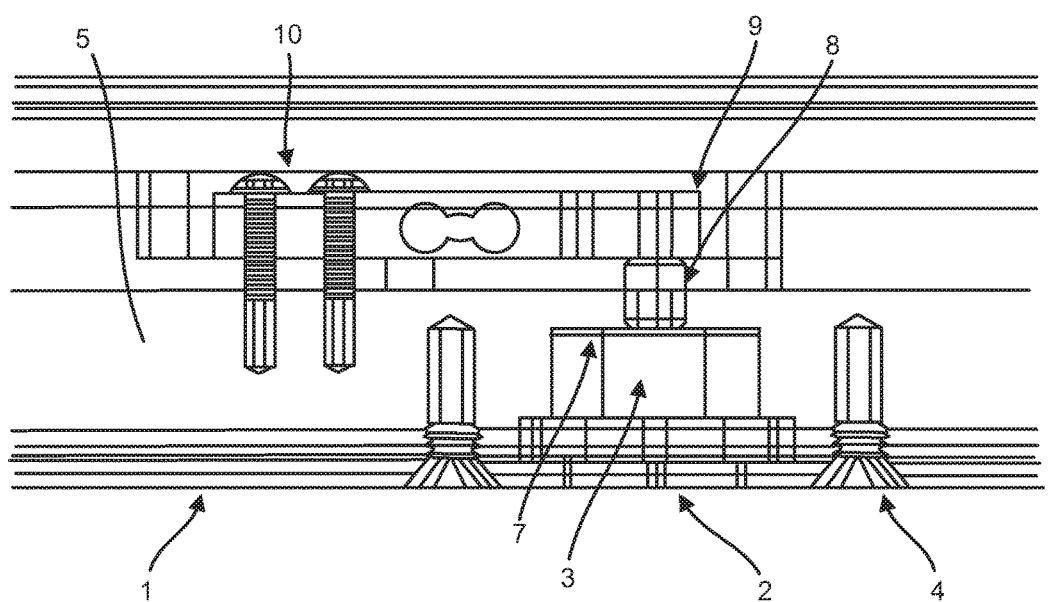
FIG. 7 illustrates a close-up side planar view of a complete assembly of the first embodiment of the elongated probe.
Figure 8:
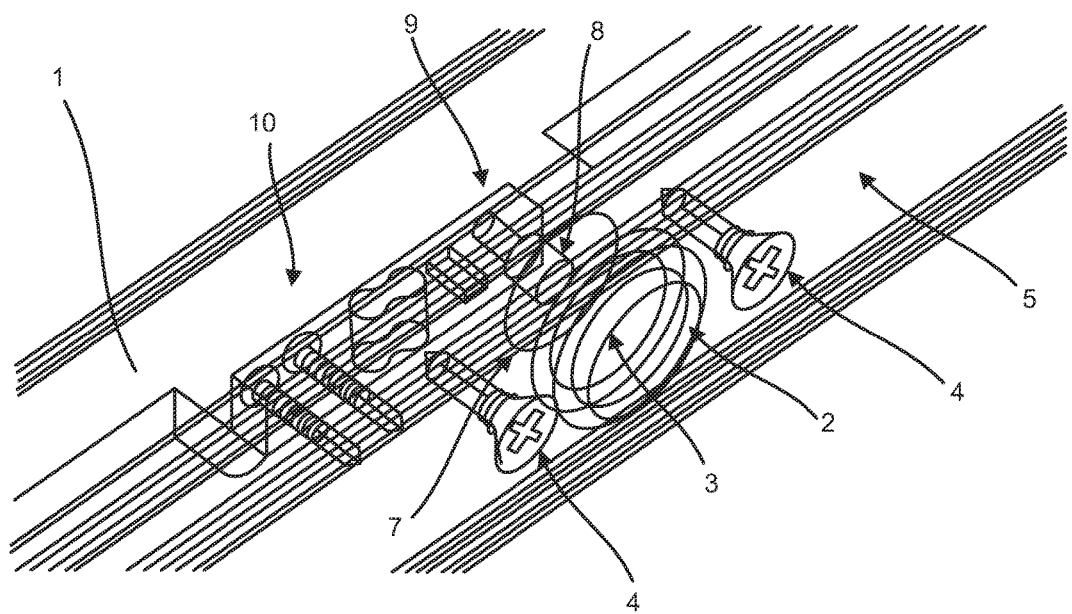
FIG. 8 illustrates a close-up perspective view of a complete assembly of the first embodiment of the elongated probe.

As illustrated in FIG. 6B, the inner frame 5 of the elongated probe 27 defines a hydrogel chamber 3 with an open side 24 and the inner wall 25 that opens to a passageway 26. The hydrogel chamber 3 receives a flexible barrier 7, having one side that is attached to the inner wall 25 with adhesive. The hydrogel chamber 3 receives the hydrogel 15. The passageway 26 receives the dowel pin 8. The dowel pin 8 is movable longitudinally through the passageway 26. A pair of screws 10 secures the load cell 9 to the inner frame 5. An end of the dowel pin 8 contacts the load cell 9. The opposite end of the dowel pin 8 contacts a flexible barrier 7. The flexible barrier 7 retains the hydrogel within the hydrogel chamber 3.

A durable, hydrophilic, and porous window 2 covers and closes the hydrogel chamber 3 and holds the hydrogel 15 within the hydrogel chamber. A second pair of screws 4 secure an outer frame 1 to the inner frame 5. The outer frame 1 defines an opening in alignment with each hydrogel chamber 3 (and its window 2). The outer frame secures to the inner frame that holds the components of one or more tensiometers disposed in spaced-apart relation within the elongated probe 27 for measuring SWT at predetermined depths based on the spacing and the number of tensiometers in the apparatus.

Wires that are secured along a channel within the inner frame 5 transmit power to the load cell(s) from batteries in the head unit and enable communication between the load cells(s) and the microcontroller in the head unit. The load cell 9 thereby senses force based on the pressure of the hydrogel 15 within the hydrogel chamber 3, depending on the volume of water absorbed by the hydrogel 15 through the window 2.

A second embodiment of the elongated probe 27 (illustrated in FIG. 10 in a side cross-sectional format), uses a linear variable differential transformer (LVDT) 12 as a sensor. The tensiometer 11 of this embodiment comprises an LVDT 12 (attached to an inner frame 5 by adhesive), a flexible barrier 7, a hydrogel chamber 3, hydrogel 15, and a window 2.

This second embodiment, like the first embodiment, has an inner and outer frame as illustrated in FIG. 6B; the inner frame 5 of the elongated probe 27 defines a hydrogel chamber 3 with an open side 24 and the inner wall 25 that opens to a passageway 26. The hydrogel chamber 3 receives a flexible barrier 7, having one side that is attached to the inner wall 25 with adhesive. The hydrogel chamber 3 receives the hydrogel 15. A portion of the side of the flexible barrier 7 that is movable longitudinally through the passageway 26 contacts the LVDT 12. The flexible barrier 7 retains the hydrogel within the hydrogel chamber 3.

A durable, hydrophilic, and porous window 2 covers and closes the hydrogel chamber 3 and holds the hydrogel 15 within the hydrogel chamber. A second pair of screws 4 secure an outer frame 1 to the inner frame 5. The outer frame 1 defines an opening in alignment with each hydrogel chamber 3 (and its window 2). The outer frame secures to the inner frame that holds the components of one or more tensiometers disposed in spaced-apart relation within the elongated probe 27 for measuring SWT at predetermined depths based on the spacing and the number of tensiometers 11 in the apparatus.

Wires 13 that are secured along a channel 14 within the inner frame 5 transmit power to the LVDT(s) from batteries in the head unit and enable communication between the LVDT(s) and the microcontroller in the head unit. The LVDT 12 thereby senses longitudinal movement or displacement based on the pressure of the hydrogel 15 within the hydrogel chamber 3, depending on the volume of water absorbed by the hydrogel 15.

A third embodiment of the elongated probe 27 (illustrated in FIG. 11 in a side cross-sectional format), uses a proximity sensor 17 as a sensor. The tensiometer 11 of this embodiment comprises a proximity sensor 17 (attached to an inner frame 5 by adhesive), a target plate 16, a flexible barrier 7, a hydrogel chamber 3, hydrogel 15, and a window 2.

This third embodiment, like the first embodiment, has an inner and outer frame as illustrated in FIG. 6B; the inner frame 5 of the elongated probe 27 defines a hydrogel chamber 3 with an open side 24 and the inner wall 25 that opens to a passageway 26. The hydrogel chamber 3 receives a flexible barrier 7, having one side that is attached to the inner wall 25 with adhesive. The hydrogel chamber 3 receives the hydrogel 15. A portion of the side of the flexible barrier 7 that is movable longitudinally through the passageway 26 attaches to the target plate 16 with adhesive. The flexible barrier 7 retains the hydrogel within the hydrogel chamber 3.

A durable, hydrophilic, and porous window 2 covers and closes the hydrogel chamber 3 and holds the hydrogel 15 within the hydrogel chamber. A second pair of screws 4 secure an outer frame 1 to the inner frame 5. The outer frame 1 defines an opening in alignment with each hydrogel chamber 3 (and its window 2). The outer frame secures to the inner frame that holds the components of one or more tensiometers 11 disposed in spaced-apart relation within the elongated probe 27 for measuring SWT at predetermined depths based on the spacing and the number of tensiometers 11 in the apparatus.

Wires 13 that are secured along a channel 14 within the inner frame 5 transmit power to the proximity sensor(s) from batteries in the head unit and enable communication between the proximity sensor(s) and the microcontroller in the head unit. The proximity sensor 17 thereby senses proximity of the target plate 16 based on the pressure of the hydrogel 15 within the hydrogel chamber 3, depending on the volume of water absorbed by the hydrogel 15.

A fourth embodiment of the elongated probe 27 (illustrated in FIG. 12 in a side cross-sectional format), uses a microelectromechanical systems (MEMS) pressure sensor 18 as a sensor. The tensiometer 11 of this embodiment comprises a MEMS pressure sensor 18 (attached to an inner frame 5 by adhesive), a hydrogel chamber 3, hydrogel 15, and a window 2.

This fourth embodiment, like the first embodiment, has an inner and outer frame as illustrated in FIG. 6B; the inner frame 5 of the elongated probe 27 defines a hydrogel chamber 3 with an open side 24 and the inner wall 25 that opens to a passageway 26. The MEMS pressure sensor 18 is received into the passageway 26 and held in place by adhesive, sealing the passageway 26. The hydrogel chamber 3 receives the hydrogel 15.

A durable, hydrophilic, and porous window 2 covers and closes the hydrogel chamber 3 and holds the hydrogel 15 within the hydrogel chamber. A second pair of screws 4 secure an outer frame 1 to the inner frame 5. The outer frame 1 defines an opening in alignment with each hydrogel chamber 3 (and its window 2). The outer frame secures to the inner frame that holds the components of one or more tensiometers 11 disposed in spaced-apart relation within the elongated probe 27 for measuring SWT at predetermined depths based on the spacing and the number of tensiometers 11 in the apparatus.

Wires 13 that are secured along a channel 14 within the inner frame 5 transmit power to the MEMS pressure sensor(s) from batteries in the head unit and enable communication between the MEMS pressure sensor(s) and the microcontroller in the head unit. The MEMS pressure sensor 18 thereby senses the pressure of the hydrogel 15 within the hydrogel chamber 3, depending on the volume of water absorbed by the hydrogel 15.

The embodiments of the elongated probes disclosed herein operate for providing SWT data at selected soil depths for evaluating whether to irrigate. The elongated probe 27 may readily be disposed in a selected ground location, such as in a vertical hole sufficiently deep for the length of the elongated probe 27. Soil backfills the hole. Upon installation, the moisture in the soil migrates through the durable, hydrophilic, and porous window 2 into the hydrophilic hydrogel particles 15 held in the hydrogel chamber 3. The sensor secured to the inner frame of the elongated probe 27 in sensing relation produces a variable signal in response to a mechanical effect originating from the degree of pressure within the hydrogel chamber.

Figure 13:
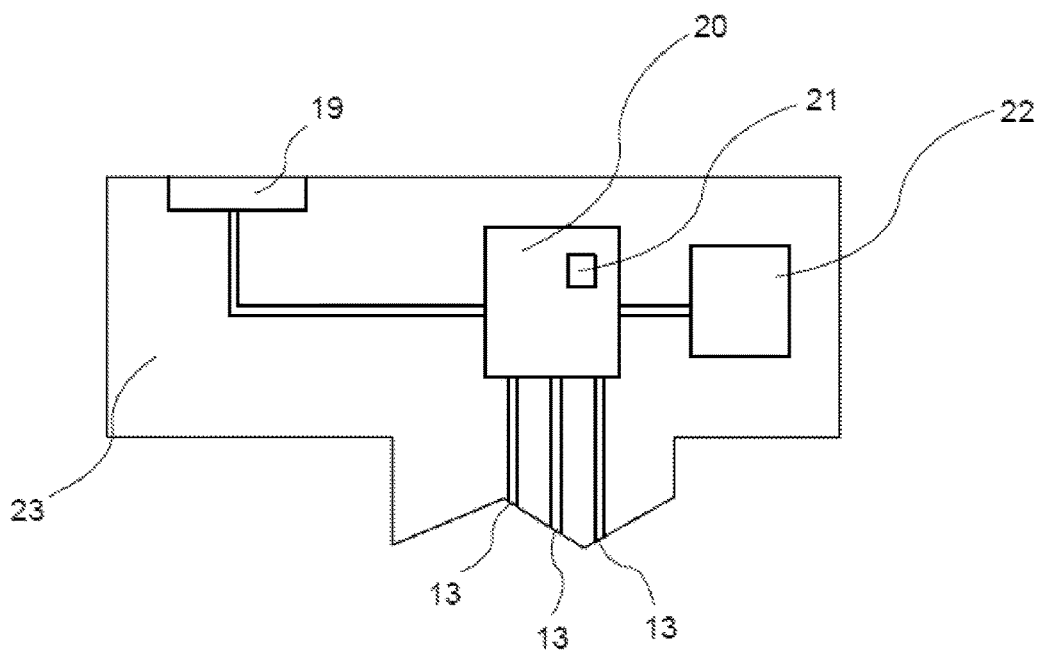
FIG. 13 illustrates a side cross-sectional view of the head unit of the present invention which is probe-agnostic meaning that it readily connects to any of the four previously-described embodiments of the elongated probe of the present invention.

The structures described above communicate the variable signal to a probe-agnostic head unit 23 (as illustrated in FIG. 13) based on a mechanical effect originating from the degree of pressure within the hydrogel chamber based on absorption through the window of soil water proximal to the window. Batteries 22 power the apparatus including the sensor(s) within the elongated probe 27. A circuit board 20 connects the electronics within the apparatus 23. Wires 13 transmit power to the sensor(s) from the battery and enable communication between the sensor(s) and the microcontroller 21. The microcontroller 21 in the head unit converts the signal from the sensor to a SWT value, based on a conversion algorithm obtained through a calibration process, and the value is either sent via a remote transmission module 19 within the head unit (when remote data transmission is needed) or displayed on a screen within the head unit 19 (when remote data transmission is not needed).

In summary, the present apparatus and method measures SWT using sensors that variously measure force (via a load cell), displacement (via an LVDT), proximity (via a proximity sensor), and pressure (via MEMS pressure sensor).

The embodiments of the present invention use as the outer enclosure for the hydrogel within the hydrogel chamber a durable, hydrophilic, and porous material, or in an alternate embodiment, aluminum oxide ceramic.

The first three embodiments of the present invention use as the inner enclosure for the hydrogel within the hydrogel chamber a flexible barrier durable, or in an alternate embodiment, as 1/32" piece of a sheet or layer of rubber.

In the present invention, hydrogel 15 is synthesized into macro-sized (~1 mm) particles to prevent leakage through the window 2. This hydrogel can consist of, but is not limited to, one of the following materials: cross-linked polyethylene glycol, cross-linked sodium polyacrylate, cross-linked polyvinyl alcohol, and cross-linked polyvinyl pyrolidone.

It is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A moisture monitoring apparatus, comprising:
   an elongated probe;
   the elongated probe having at least one tensiometer, each tensiometer comprising:
      a hydrogel chamber formed in the elongated probe and having an inner wall and an open side;
      hydrogel comprising a plurality of millimeter-sized hydrophilic particles received into the hydrogel chamber through its open side;
      a durable, hydrophilic, and porous window attached to the elongated probe in sealing closing relation overlying the open side of the hydrogel chamber and an inner face of the window in bearing contact with a portion of the hydrogel for holding the hydrogel within the hydrogel chamber; and
      a sensor secured to the elongated probe in sensing relation for measuring a mechanical effect originating from the pressure within the hydrogel chamber;
   a microcontroller responsive to the signal from the sensor of a respective tensiometer for reporting a determined moisture level proximal to the window, and
   whereby moisture-related decisions are directed by an evaluation of an observed moisture level detected by the tensiometer(s) within the apparatus.

2. The moisture monitoring apparatus as recited in claim 1, further comprising:
   the microcontroller receiving the signal from the sensor of a respective tensiometer and analyzing the detected signal and reporting a determined moisture level proximal to the window of the tensiometer, and
   whereby moisture-related decisions are directed by an evaluation of an observed moisture level detected by the tensiometer(s) within the apparatus.

3. The moisture monitoring apparatus as recited in claim 1, wherein
   the sensor comprises a load cell attached to the elongated probe in sensing relation to the inner wall of the hydrogel chamber;
   the inner wall defining an opening to a passageway;
   a flexible barrier recessed in the hydrogel chamber for covering the opening in the inner wall; and
   linkage between the flexible barrier and the load cell, and
   whereby the load cell generates a signal in response to the force received through the flexible barrier originating from the pressure within the hydrogel chamber according to the amount of moisture absorbed from the opposite end of the window.

4. The moisture monitoring apparatus as recited in claim 1, wherein
   the sensor comprises a linear variable differential transformer (LVDT) attached to the elongated probe in sensing relation to the inner wall of the hydrogel chamber;
   the inner wall defining an opening to a passageway;
   a flexible barrier recessed in the hydrogel chamber for covering the opening in the inner wall; and
   linkage between the flexible barrier and the LVDT, and
   whereby the LVDT generates a signal in response to the displacement received through the flexible barrier originating from the pressure within the hydrogel chamber according to the amount of moisture absorbed from the opposite end of the window.

5. The moisture monitoring apparatus as recited in claim 1, wherein
   the sensor comprises a proximity sensor attached to the elongated probe in sensing relation to the inner wall of the hydrogel chamber;
   the inner wall defining an opening to a passageway;
   a flexible barrier recessed in the hydrogel chamber for covering the opening in the inner wall; and
   a target plate linked to the flexible barrier and disposed in the passageway for longitudinal movement therein,
   a proximity sensor mounted at the opposing end of the passageway, and
   whereby the proximity sensor generates a signal in response to the proximity of the target plate according to the pressure within the hydrogel chamber according to the amount of moisture absorbed from the opposite end of the window.

6. The moisture monitoring apparatus as recited in claim 1, the elongated probe further comprising an outer frame secured to an inner frame telescopically received therein.

7. The moisture monitoring apparatus as recited in claim 1, wherein the microcontroller is configured with software instructions for evaluating the signal relative to predetermined moisture values to determine moisture proximal to the sensor.

8. The moisture monitoring apparatus as recited in claim 1, whereupon
   the hydrogel inside the hydrogel chamber, absorbing moisture proximal to the opposite end of the window and expanding to reach a hydrostatic pressure equilibrium with said moisture, increases the pressure inside the hydrogel chamber, which produces a mechanical effect measurable by the sensor; and
   the sensor sends a voltage representative of the mechanical effect to the microcontroller that converts the voltage to a moisture level proximal to the window per the voltage registered by the sensor.

9. The moisture monitoring apparatus as recited in claim 1,
wherein the microcontroller electrically communicates with the sensor for receiving periodically the signal therefrom and evaluating the signal, and
wherein the sensor sending the signal as a voltage to the microcontroller is configured to evaluate a mechanical effect originating from the pressure within the hydrogel chamber based on the amount of water absorbed by the hydrogel into the hydrogel chamber through the window.

10. The moisture monitoring apparatus as recited in claim 1, wherein
the sensor is a microelectromechanical (MEMS) pressure sensor attached to the elongated probe in sensing relation to the inner wall of the hydrogel chamber; and
whereby the MEMS pressure sensor generates a signal in response to the pressure within the hydrogel chamber according to the amount of moisture absorbed from the opposite end of the window.

11. The moisture monitoring apparatus as recited in claim 1, wherein the elongated probe includes two or more tensiometers disposed in spaced-apart relation, for measuring soil water tension at respective depths in a soil profile, upon positioning the apparatus within soil.

12. The moisture monitoring apparatus as recited in claim 11, wherein each one of the tensiometers is associated with a respective unique identifier, which identifier accompanies the signal communicated to the microcontroller so that evaluations may occur relative to a vertical profile within the soil at spaced-apart depths.

13. The moisture monitoring apparatus as recited in claim 1, wherein the tensiometer electrically connects to an automated irrigation control device for irrigation control purposes.

14. The moisture monitoring apparatus as recited in claim 13, further comprising a wireless communicator that communicates the signal of the sensor to a receiver.

15. The moisture monitoring apparatus as recited in claim 1, further comprising a resilient gasket seated between the window and the hydrogel chamber.

16. A method for providing a signal that indicates soil water tension for evaluating whether to irrigate, comprising the steps of:
  (a) providing an apparatus including an elongated probe with at least one tensiometer, each tensiometer comprising:
  a hydrogel chamber formed in the elongated probe and having an inner wall and an open side;
  hydrogel comprising a plurality of millimeter-sized hydrophilic particles received into the hydrogel chamber through its open side;
  a durable, hydrophilic, and porous window attached to the elongated probe in sealing closing relation overlying the open side of the hydrogel chamber and an inner face of the window in bearing contact with a portion of the hydrogel for holding the hydrogel within the hydrogel chamber; and
  a sensor secured to the elongated probe in sensing relation for detecting a variable signal caused by a mechanical effect originating from the pressure within the hydrogel chamber based on the amount of water absorbed by the hydrogel into the hydrogel chamber through the window
  (b) providing a second part of the apparatus, a head unit (that connects to the elongated probe such as by mated threads, press fit, or similar, providing a leak proof joinder of the two components) comprising:
  batteries to power the apparatus;
  a microcontroller to control the apparatus such as by determining when the apparatus enters battery-saving mode and when the apparatus exits battery-saving mode to collect and communicate a signal from a sensor within a tensiometer in the elongated probe;
  a circuit board; and
  a remote transmission module (for when remote data transmission is needed); or a display screen (for when remote data transmission is not needed)
  (c) inserting the apparatus into a selected location in a ground surface to dispose the elongated probe and its tensiometer(s) below the surface of the soil;
  (d) acquiring from the sensor within a tensiometer a variable signal originating from the pressure within the hydrogel chamber based on the amount of water absorbed by the hydrogel into the hydrogel chamber through the window;
  (e) displaying on a display screen within the head unit or sending via a remote transmission module within the head unit a determined SWT at a soil depth associated with a respective tensiometer, and
  whereby soil irrigation decisions are directed by an evaluation of an observed soil water tension detected by the moisture monitoring apparatus disposed in the ground location.

17. The method as recited in claim 16, further comprising the steps of:
  receiving by a communicator the signal from the sensor of a respective tensiometer; and
  communicating the signal to the microcontroller configured for analyzing the detected pressure and reporting a determined soil water tension at a soil depth associated with the tensiometer, and
  whereby soil irrigation decisions are directed by an evaluation of an observed soil water tension detected by the moisture monitoring apparatus disposed in the ground location.

18. The method as recited in claim 16, wherein step (c) further comprises
  communicating the soil-moisture-induced force by a dowel pin disposed in a passageway for longitudinal movement therein,
  a first end of the dowel pin in contact with a first side of a flexible barrier recessed in the hydrogel chamber for covering an opening in the inner wall to the passageway,
  the sensor comprising a load cell attached to the elongated probe sensing relation to the inner wall of the hydrogel chamber,
  a second end of the dowel pin in contact with a load cell, and
  whereby the load cell generates a signal in response to the force applied by the dowel pin based on the soil-moisture-induced pressure of the hydrogel on the flexible barrier according to the amount of moisture absorbed from the soil through the window.

19. The method as recited in claim 16, wherein step (c) further comprises
  communicating the soil-moisture-induced pressure by a flexible barrier, part of which is disposed at the opening of a passageway for longitudinal movement therein,
  the flexible barrier recessed in the hydrogel chamber for covering the opening, the sensor comprising a linear variable differential transformer (LVDT) attached to the elongated probe in sensing relation to the inner wall of the hydrogel chamber and a portion of the flexible barrier allowed to move within in the passageway in contact with the LVDT, and whereby the LVDT generates a signal in response to the displacement applied by the flexible barrier originating from the pressure within the hydrogel chamber based on the amount of water absorbed by the hydrogel into the hydrogel chamber through the window.

20. The method as recited in claim 16, wherein step (c) further comprises sensing proximity of a target plate disposed in a passageway for longitudinal movement therein, the passageway closed at one end by a flexible barrier recessed in a hydrogel chamber to cover an opening in an inner wall to the passageway, the sensor comprising a proximity sensor attached to the elongated probe in alignment with the passageway, and whereby the proximity sensor generates a signal in response to a position of the target plate as determined by the pressure originating from within the hydrogel chamber based on the amount of water absorbed by the hydrogel into the hydrogel chamber through the window.

21. The method as recited in claim 16, wherein step (c) further comprises sensing pressure within the hydrogel chamber with a microelectromechanical systems (MEMS) pressure sensor, and whereby the MEMS pressure sensor generates a signal in response to the pressure within the hydrogel chamber based on the amount of water absorbed by the hydrogel into the hydrogel chamber through the window.

* * * * *